United States Patent
Dijksman et al.

(10) Patent No.: US 9,744,139 B2
(45) Date of Patent: Aug. 29, 2017

(54) MODULAR INGESTIBLE DRUG DELIVERY CAPSULE

(75) Inventors: Johan Frederik Dijksman, Eindhoven (NL); Anke Pierik, Eindhoven (NL); Frits Tobi De Jongh, Eindhoven (NL); Jeff Shimizu, Cortlandt Manor, NY (US); Hans Zou, Windsor, NJ (US); Lucian Remus Albu, Forest Hills, NY (US); Olaf Weiner, Eindhoven (NL)

(73) Assignee: Stoco 10 GmbH (DE)

( * ) Notice: Subject to any disclaimer, the term of this patent is extended or adjusted under 35 U.S.C. 154(b) by 561 days.

(21) Appl. No.: 13/262,841

(22) PCT Filed: Apr. 2, 2010

(86) PCT No.: PCT/IB2010/051453
§ 371 (c)(1),
(2), (4) Date: Jan. 16, 2012

(87) PCT Pub. No.: WO2010/116312
PCT Pub. Date: Oct. 14, 2010

(65) Prior Publication Data
US 2012/0116358 A1    May 10, 2012

Related U.S. Application Data

(60) Provisional application No. 61/167,240, filed on Apr. 7, 2009.

(51) Int. Cl.
*A61K 9/48* (2006.01)
*A61K 9/00* (2006.01)
*A61M 31/00* (2006.01)

(52) U.S. Cl.
CPC .......... *A61K 9/4808* (2013.01); *A61K 9/0009* (2013.01); *A61K 9/0097* (2013.01); *A61M 31/002* (2013.01)

(58) Field of Classification Search
CPC .. A61K 9/0009; A61K 9/0097; A61B 5/4839; A61B 5/4255; A61M 31/002;
(Continued)

(56) References Cited

U.S. PATENT DOCUMENTS

| 4,564,363 A | 1/1986 | Bagnall et al. |
| 4,572,403 A | 2/1986 | Benaroya |

(Continued)

FOREIGN PATENT DOCUMENTS

| CN | 1958090 | | 5/2007 |
| DE | 3339323 | * | 5/1985 |

(Continued)

OTHER PUBLICATIONS

EPO English Translation of DE3339323, Apr. 4, 2016.*
(Continued)

*Primary Examiner* — Imani Hayman
*Assistant Examiner* — Laura Schell
(74) *Attorney, Agent, or Firm* — Emerson Thomson Bennett, LLC (57) ABSTRACT

An ingestible capsule (10) is provided for delivery of a drug, the capsule (10) comprises a first module (11) and a second module (12). The first module (11) has at least one drug compartment (13) for comprising an amount of the drug. The drug compartment (13) is sealed by a foil (14) with an embedded conducting heating wire (15). The second (12) module comprises electronics (18) for providing an electrical pulse to the heating wire (15) in order to open the drug compartment (13) by melting the foil (14). The first module (11) and second module (12) comprise interoperable connection means (19) for securing the first module (11) to the second module (12) such that the heating wire (15) is electronically coupled to the electronics (18).

19 Claims, 5 Drawing Sheets

(58) Field of Classification Search
CPC .......... A61M 5/14276; A61M 2205/50; A61M 5/172; A61M 31/00; A61M 2205/0244; A61D 7/00
USPC .......................................... 604/891.1, 892.1
See application file for complete search history.

(56) References Cited

U.S. PATENT DOCUMENTS

| | | | |
|---|---|---|---|
| 4,642,230 A * | 2/1987 | Whitehead | A61M 31/002 424/409 |
| 4,814,180 A | 3/1989 | Eckenhoff et al. | |
| 5,071,040 A | 12/1991 | Laptewicz, Jr. | |
| 5,170,801 A | 12/1992 | Casper et al. | |
| 5,279,607 A | 1/1994 | Schentag et al. | |
| 5,318,557 A | 6/1994 | Gross | |
| 5,423,779 A | 6/1995 | Yeh | |
| 5,853,386 A | 12/1998 | Davis et al. | |
| 6,001,090 A * | 12/1999 | Lenhart | 604/890.1 |
| 6,053,899 A | 4/2000 | Slanda et al. | |
| 6,182,941 B1 | 2/2001 | Scheurenbrand et al. | |
| 6,423,779 B2 | 7/2002 | Sue et al. | |
| 6,632,216 B2 | 10/2003 | Houzego et al. | |
| 6,699,214 B2 | 3/2004 | Gellman | |
| 6,776,165 B2 | 8/2004 | Jin | |
| 6,800,060 B2 | 10/2004 | Marshall | |
| 6,929,636 B1 | 8/2005 | von Alten | |
| 7,014,640 B2 | 3/2006 | Kemppainen et al. | |
| 7,647,090 B1 * | 1/2010 | Frisch | A61B 1/00105 600/109 |
| 8,021,357 B2 | 9/2011 | Tanaka et al. | |
| 8,100,889 B2 | 1/2012 | Kawano et al. | |
| 8,308,681 B2 | 11/2012 | Slocum et al. | |
| 8,317,681 B1 * | 11/2012 | Gazdzinski | 600/118 |
| 2003/0020810 A1 * | 1/2003 | Takizawa et al. | 348/68 |
| 2003/0213495 A1 | 11/2003 | Fujita et al. | |
| 2004/0121486 A1 * | 6/2004 | Uhland | A61M 25/0082 436/174 |
| 2004/0242962 A1 | 12/2004 | Uchiyama | |
| 2004/0267240 A1 | 12/2004 | Gross et al. | |
| 2005/0222537 A1 | 10/2005 | Dinsmoor et al. | |
| 2006/0100608 A1 * | 5/2006 | Uhland et al. | 604/891.1 |
| 2006/0155174 A1 | 7/2006 | Glukhovsky et al. | |
| 2007/0138027 A1 | 6/2007 | Dinsmoor et al. | |
| 2010/0086767 A1 * | 4/2010 | Thottupurathu | B29C 47/0004 428/316.6 |

FOREIGN PATENT DOCUMENTS

| | | |
|---|---|---|
| JP | 2001526939 | 12/2001 |
| JP | 2002532162 | 10/2002 |
| JP | 2003520108 | 7/2003 |
| JP | 2005536307 | 12/2005 |
| WO | WO2005025647 | 3/2005 |
| WO | WO2006021932 | 3/2006 |
| WO | WO2006056944 | 6/2006 |
| WO | WO2006077529 | 7/2006 |
| WO | WO2008029372 | 3/2008 |
| WO | WO2008036199 | 4/2008 |
| WO | WO2008062335 | 5/2008 |

OTHER PUBLICATIONS

Translated Chinese Office Action mailed Jan. 15, 2013 for Chinese patent application No. 201080015953.5, a counterpart foreign application of U.S. Appl. No. 13/262,841, 17 pages.
Translated Chinese Office Action mailed Jan. 21, 2013 for Chinese patent application No. 201080040663.8, a counterpart foreign application of U.S. Appl. No. 13/300,111, 8 pages.
Translated Chinese Office Action mailed Mar. 14, 2013 for Chinese patent application No. 200980112018.8, a counterpart foreign application of U.S. Appl. No. 12/933,891, 12 pages.
Chinese Office Action mailed May 13, 2013 for Chinese patent application No. 201080015284.1, a counterpart foreign application of U.S. Appl. No. 13/262,861, 11 pages.
Translated Japanese Office Action mailed Apr. 16, 2013 for Japanese Patent Application No. 2011-514179, a counterpart foreign application of U.S. Appl. No. 12/992,305, 9 pages.
Translated Japanese Office Action mailed Apr. 30, 2013 for Japanese patent application No. 2010-546431, a counterpart foreign application of U.S. Appl. No. 12/867,888, 4 pages.
Kompella, et al., "Delivery System for Penetration Enhancement of Peptide and Protein Drugs: Design Considerations", Advanced Drug Delivery Reviews, vol. 46, 2001, pp. 211-245.
Paine, et al., "Characterization of Interintestinal and Intraintestinal Variations in Human CYP3A-Dependent Metabolism", The Journal of Pharmacology and Experimental Therapeutics, vol. 283, No. 3, 1997, pp. 1552-1562.
Siccardi, et al., "Regulation of Intestinal Epithelial Function: A Link Between Opportunities for Macromolecular Drug Delivery and Inflammatory Bowel Disease", Advanced Drug Delivery Reviews, vol. 57, 2005, pp. 219-235.
Translated Japanese Office Action mailed Apr. 23, 2013 for Japanese patent application No. 2012-524322, a counterpart foreign application of U.S. Appl. No. 13/390,111, 6 pages.
Office action for U.S. Appl. No. 12/992,305, mailed on Jul. 16, 2013, Zou et al., "Device for Delivery of Powder Like Medication in a Humid Environment", 14 pages.
Non-Final Office Action for U.S. Appl. No. 11/720,242, mailed on Jul. 3, 2013, Gerardus Rudolph Langereis et al., "Electronically Controlled Pill and System Having at Least One Sensor for Delivering at Least One Medicament", 22 pages.
Transated Japanese Office Action mailed Feb. 4, 2014 for Japanese patent application No. 2012-504117, a counterpart foreign application of U.S. Appl. No. 13/262,841, 5 pages.

* cited by examiner

MODULAR INGESTIBLE DRUG DELIVERY CAPSULE

FIELD OF THE INVENTION

This invention relates to an ingestible capsule for delivery of a drug, the capsule comprising a first module with at least one drug compartment for comprising an amount of the drug, a second module with electronics for effectuating the delivery of the drug from the drug compartment into an environment of the capsule, the first and second module comprising interoperable connection means for securing the first module to the second module.

BACKGROUND OF THE INVENTION

Such an ingestible capsule is known from the international patent application WO 2008/062335, wherein a first part comprising a drug reservoir is secured to a second part comprising a driving mechanism. The drug reservoir has a flexible wall and the driving mechanism has a piston. The driving mechanism is controlled electronically. When the piston is driven into the flexible wall, the pressure inside the reservoir increases and the drug is pushed out of a small opening in the drug reservoir. This displacement controlled pressure based drug delivery device works best with drugs in a more or less liquid form, such as a solution, suspension, emulsion, gel or pasta.

However, for the treatment of many diseases, it would be of great value to have the drug available in powder form. In powder form, the drug has a longer shelf life and is much less prone to degradation. In powder form it often has the highest content of active material per unit volume. The drug delivery device of WO 2008/062335 is not very suitable for delivering the drug in powder form, because a powder is not easily pushed through a small hole.

OBJECT OF THE INVENTION

It is an object of the invention to provide a modular drug delivery device as described in the opening paragraph, which drug delivery device is suitable for the delivery of drugs in powder form.

SUMMARY OF THE INVENTION

According to a first aspect of the invention, this object is achieved by providing an ingestible capsule for delivery of a drug, the capsule comprising a first module and a second module. The first module comprises at least one drug compartment for comprising an amount of the drug, the drug compartment being sealed by a foil with an embedded conducting heating wire. The second module comprises electronics for providing an electrical pulse to the heating wire in order to open the drug compartment by breaking the foil. The first module and second module comprise interoperable connection means for securing the first module to the second module such that the heating wire is electronically coupled to the electronics.

At a certain moment, when the capsule is somewhere in the gastrointestinal system, the electronics provide an electrical pulse for initiating the delivery of the drug. Upon the electrical pulse, the wire is heated to such a high temperature that the foil melts along the line defined by the heating wire, thereby opening the drug compartment and releasing the medication. Alternatively, the heating of the foil may cause it to crack under surface tension. The heating wire may be provided inside or attached to the foil. The placement of the heating wire relative to the foil should at least be such that the foil is melted when a sufficiently intense electrical pulse or series of pulses runs through the heating wire. The powder particles are then exposed to the content of the gastrointestinal system and are washed out of the drug compartment by the fluid in the direct environment of the capsule. The peristalsis and mixing motions of the intestines will assist the emptying of the drug compartment and will dissolve the drug. The dissolved drug may pass the gastrointestinal barrier or will become effective directly on the spots where it is needed.

Conductive parts on the first and second module, which conductive parts are respectively coupled to the heating wire and the electronics, are in contact with each other when the first module is coupled to the second module. The coupling between the two modules may, e.g., be realized using sliding contacts or a screw thread.

Preferably, the electronics comprise at least one capacitor for increasing an intensity of the electrical pulses. Because of size limitation for ingestible capsules, the power source, e.g. a battery, should not be too large. A smaller power source delivers relatively low power. Using one or more capacitors may help to considerably increase the intensity of the electrical pulses.

Preferably, the inner wall of the drug compartment is provided with an anti-sticking layer in order to assist the washing out of all drugs from the drug compartment after the foil breaks. For example, the wall may be coated with Teflon to prevent the powder from sticking to the wall.

It is a big advantage of the capsule according to the invention, that it can easily be equipped with additional drug compartments, having their own sealing foil and respective conductive heating wire. A capsule with multiple compartments may be used for delivering discrete amounts of drugs at different moments in time or positions within the gastrointestinal system. The multiple compartments may also be used for storing and delivering different drugs or other substances.

These and other aspects of the invention are apparent from and will be elucidated with reference to the embodiments described hereinafter.

DETAILED DESCRIPTION OF THE INVENTION

Figure 1:
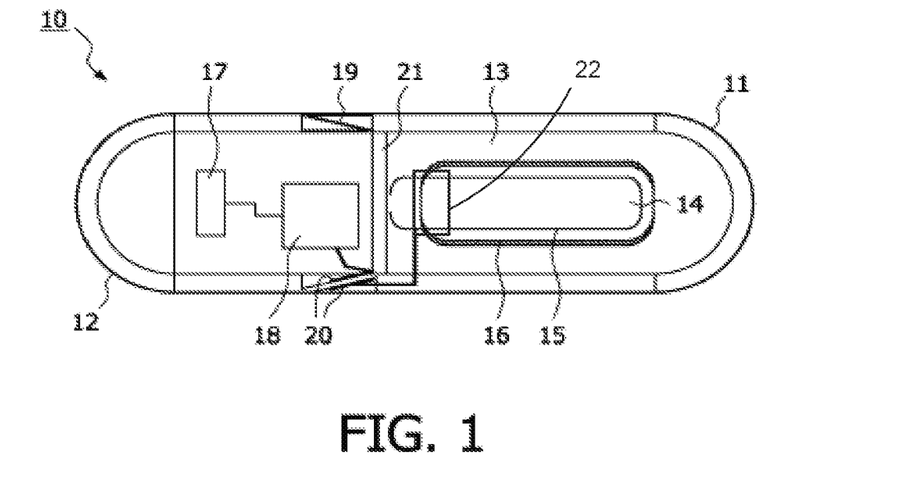
FIG. 1 shows an ingestible capsule according to the invention.

FIG. 1 shows an ingestible capsule 10 according to the invention. The capsule 10 comprises a first module 11 and a second module 12. The first module 11 comprises a drug compartment 13, filled with a drug. The drug may be provided in, e.g., a liquid form, dissolved in water, as a gel, as a pasta or encapsulated in micro capsules. Preferably, the drug is provided in powder form. The use of powder has some important advantages over the use of other types of drugs. For example, drugs in powder form have a longer shelf life and are much less prone to degradation. In powder form it often has the highest content of active material per unit volume. Some drugs are only available in powder form, e.g., because a drug or a specific combination of drugs may not be soluble in a suitable liquid. During development of new drugs, often the compound is only available in minute quantities of powder.

The drug compartment 13 has a window 16 for delivering the drug to the environment. In FIG. 1, only one window 16 is shown, but the compartment may comprise more windows. The window 16 is sealed by a foil 14 with an embedded heating wire 15. The foil 14 is made of a material that breaks when heated above a threshold temperature. For example, the foil is made of a plastic such as low density polyethylene (LDPE). The foil 14 may be covered with a high barrier layer such as polychlorotrifluoroethylene (PTCFE). The heating wire 15 comprises a conducting material which heats when an electrical current runs through. For example, the heating wire 15 is a thin copper wire or a printed electrically conducting trace. When the heating wire 15 is heated above a certain temperature, the foil 14 breaks along a line defined by the heating wire 15. To reduce the amount of energy needed for breaking the foil 14, the heating wire 15 should be laid out along a line of maximum tension of the foil 14. The breaking of the foil 14 causes the window 16 to open. The heating wire 15 may be provided inside or attached to the foil 14. The placement of the heating wire 15 relative to the foil 14 should at least be such that the foil 14 is melted when a sufficiently intense electrical pulse or series of pulses runs through the heating wire 15.

Due to diffusion, peristaltic and mixing movements of the gastrointestinal tract, the drug is washed out of the drug compartment 13. Inner walls of the drug compartment may be coated with an anti-sticking layer, e.g. comprising Teflon, to facilitate the washing out of the drug. Preferably, the window 16 is relatively large in order to aid the washing out of the drug.

The second module 12 comprises electronics 18 for controlling the moment of delivery of the drugs. The electronics 18 are arranged for providing an electrical pulse to the heating wire 15 when the drug is due to be delivered. The electronics 18 may comprise a clock for delivering the drug at a predetermined moment. Alternatively, environmental conditions may trigger the drug delivery. All kinds of sensors for registering environmental conditions (e.g. pH, temperature, presence of certain amounts of specific substances) may provide information to the electronics 18 for determining when the drug should be delivered. The second module 12 may further comprise a receiver or transmitter/receiver for communicating with external control devices. The electronics 18 are powered by a battery 17. For sufficiently heating of the heating wire 15, an intense electrical pulse may be needed. Such an intense electrical pulse may be delivered by a sufficiently powerful battery 17, but such a battery 17 may be too big for use in an ingestible capsule. The electronics 18 therefore, preferably comprise one or more capacitors for that can be charged by the battery 17 and are arranged for delivering a sufficiently intensive electrical pulse (or sequence of pulses) to the heating wire 15.

To provide the possibility to check whether the foil 14 is broken, an indicator conducting trace 22 may be added to the foil 14. This indicator trace 22 may be electrically conducting and may run at least in one position orthogonal to the heating wire 15 so that breaking of foil 14 along the heating wire 15 leads to opening of the indicator trace 22. The electronics 18 may read the foil status by checking whether the indicator trace 22 is open or close. Alternatively, the electronics 18 may be configured to detect the breaking of the heating wire 15 itself.

The modules 11, 12 are connected to each other by the connection means 19. In this embodiment the connection means are sliding contacts 19. The first module 11 slides into the second module 12, such that the modules 11, 12 together form one capsule 10. Preferably, the connecting means 19 are arranged such that the two modules 11, 12 are clamped or clicked together. Alternatively, the connection is, e.g., fixed using an adhesive or the connection means 19 are merged by melting (part of) the material of the connection means 19. The connection means 19 comprise conductive elements 20. The conductive elements 20 are arranged in such a way that, after assembling the capsule 10 by connecting the connection means 19, the conductive elements 20 of the different modules 11, 12 are in contact with each other. The conductive elements 20 in the first module 11 are coupled to the heating wire 15. The conductive elements 20 of the second module 12 are coupled to the electronics. The assembling of the capsule 10 thus results in coupling the heating wire 15 to the electronics 18 and makes the capsule 10 ready for use.

Before assembling the capsule 10, the drug compartment 13 is filled with a drug. Then the first module 11 is closed using the lid 21. The module 11 with the filled drug compartment 13 is then connected to the second module 12. The modular structure of the capsule 10 makes it possible to combine the second module 12 with a large variety of first modules 11. Depending on the intended use of the capsule 10, the first module 11 may be provided in lots of different designs and filled with lots of different drugs or combinations of drugs. The capsule 10 according to the invention is therefore very useful for research applications for which only a limited amount of test capsules is needed.

Figure 2:
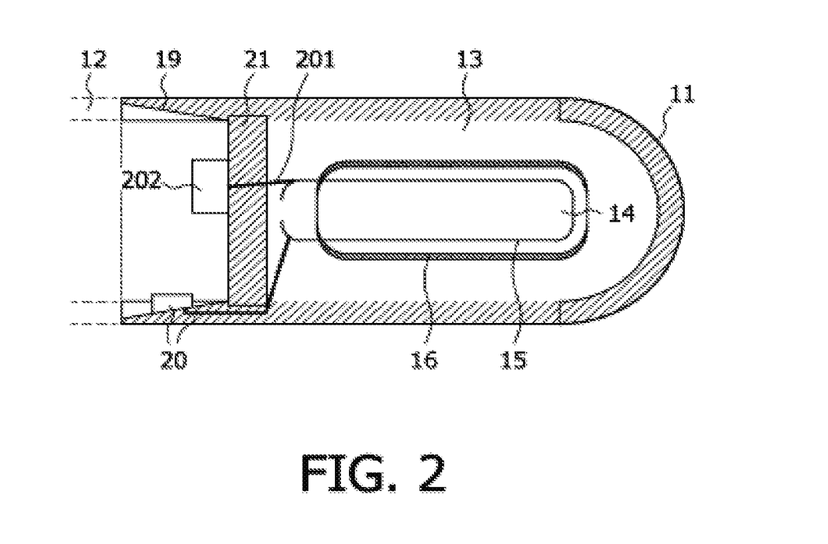
FIG. 2 shows a first module and connection means of another capsule according to the invention.

FIG. 2 shows a first module 11 and connection means 19 of another capsule 10 according to the invention. Like in FIG. 1, the connection means 19 in this embodiment comprise conductive elements 20 for electrically coupling of the two modules 11, 12 at the circumference of the capsule 10. Alternatively, the connections between the modules 11, 12 are provided in the lid. Pins 201 are integrated in the lid 21, which pins 201 are arranged for being plugged into sockets 202 of the second module 12. In the lid 21 electrical connections are provided to the heating wires 15 in the foil 14.

The electrical connection between the heating wire 15 and the electronics 18 can be arranged in many different ways. Some examples, wherein the connection means 19 comprise conductive elements 20 for establishing the electrical connection are provided in FIGS. 3, 4 and 5.

Figure 3:
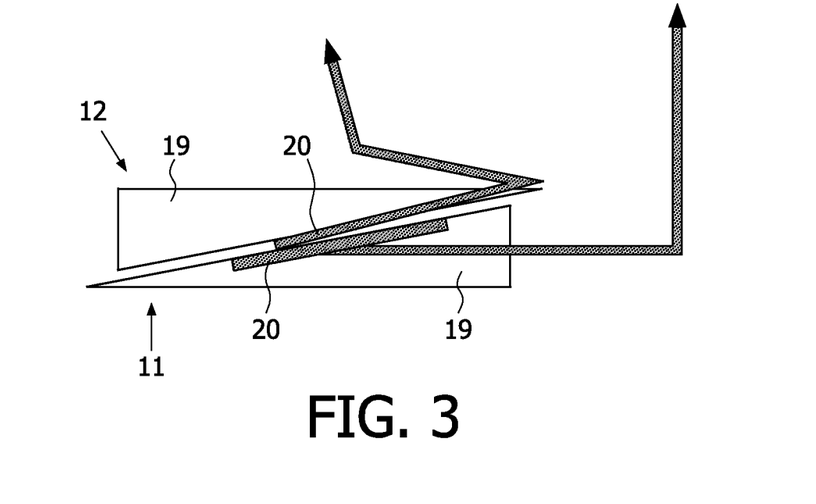
FIG. 3 shows an example of sliding contact connection means for use in a capsule according to the invention.

FIG. 3 shows an example of sliding contact connection means 19 for use in a capsule 10 according to the invention. This example is nothing more than an enlarged view of the connection means 19 of the embodiment of FIG. 1. By sliding the connection means 19 of the first module 11 over the connection means of the second module 12, the conductive 20 elements in both modules 11, 12 are brought into contact. the arrows in the FIG. respectively point to the electronics 18 and the heating wire 15.

Figure 4:
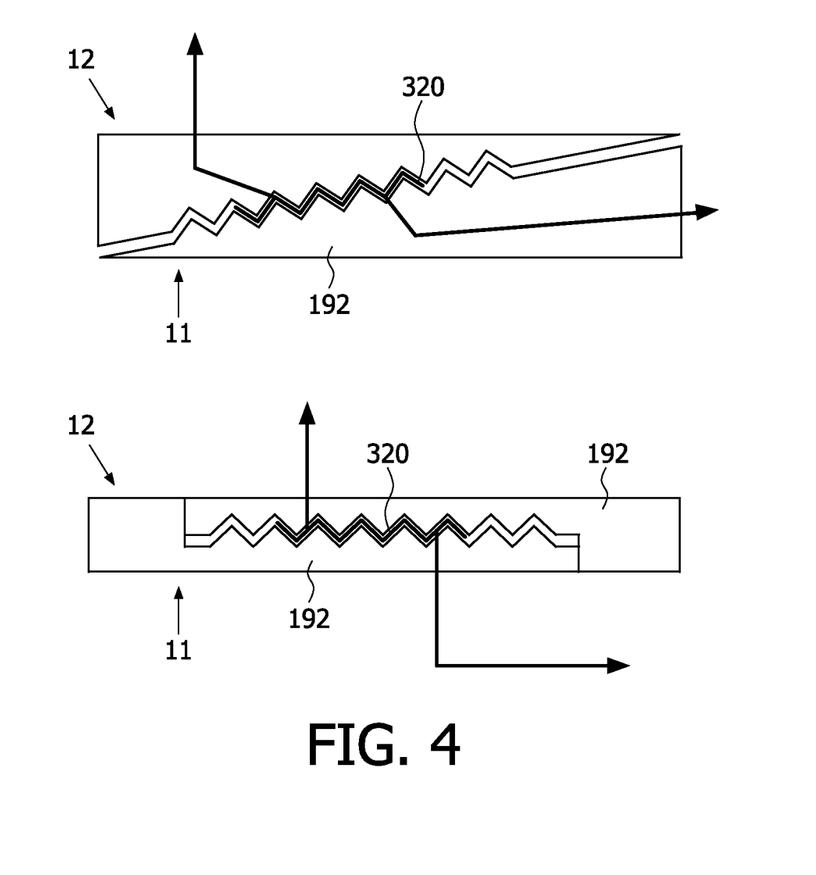
FIG. 4 shows two examples of threaded connection means for use in a capsule according to the invention.

FIG. 4 shows two examples of threaded connection means 192 for use in a capsule 10 according to the invention. The threaded connection means 192 allow for a very secure fixation of the modules 11, 12. A layer of conductive material 320 is attached to the inside of the threads. This conductive material 320 realizes the electrical connection between the two modules 11, 12.

Figure 5:
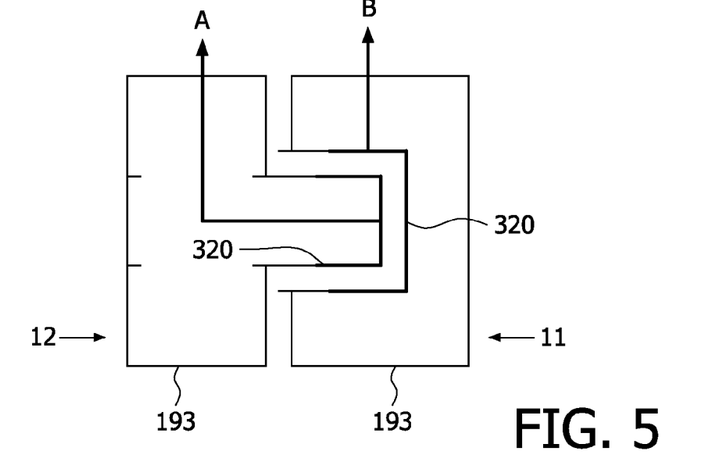
FIG. 5 shows an example of further connection means for use in a capsule according to the invention.

FIG. 5 shows an example of further connection means 193 for use in a capsule 10 according to the invention. Here, a protrusion in the connection means 193 of the second module 12 is inserted in a recess of the connection means 193 of the first module 11.

Figure 6A:
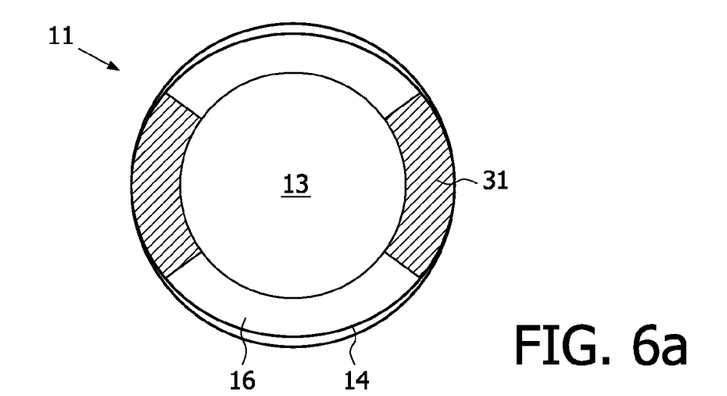
FIGS. 6a, 6b, 6c and 6d show cross sections of capsules with one or more drug compartments.

FIGS. 6a, 6b, 6c and 6d show cross sections of capsules 10 with one or more drug compartments. The cross section is made through the first module 11, in such a way that the inside of the drug compartment(s) 13 are visible. In FIG. 6a, a first module 11 is shown, having only one drug compartment 13. The drug compartment 13 has two windows 16 for delivery of the drug to the environment. Both windows 16 are closed by a seal. The compartment walls 31 also form the walls of the first module 11. The walls 31 may have an anti-sticking layer applied to its surface at the inside of the drug compartment in order to facilitate the washing out of the drugs by the environmental fluid.

Figure 6B:
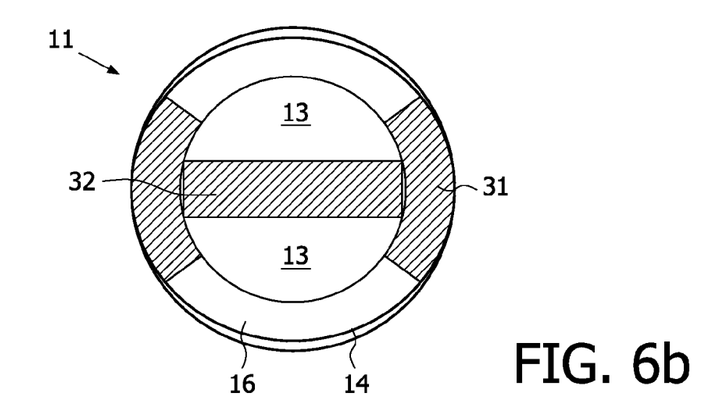

In FIG. 6b, the drug compartment 13 is divided in two by a separation wall 32. As a result, the module 11 has two drug compartments 13. Each drug compartment 13 has its own window 16 for releasing the drug. For use of the capsule 10 according to the invention, the different drug compartments 13 may be filled with the same or different kind of drugs. It is also possible to fill the different drug compartment 13 with different amounts of drug. One of the drug compartments 13 may comprise additional sensors or electronics for providing additional control over the release of drugs in the other drug compartment 13. This may especially be useful for research purposes, e.g., when the electronics 18 in the second module do not have all desired functionality. These additional sensors and electronics may be powered by the battery 17 in the second module, via the electrical contact 20 provided by the connection means 19.

Figure 6C:
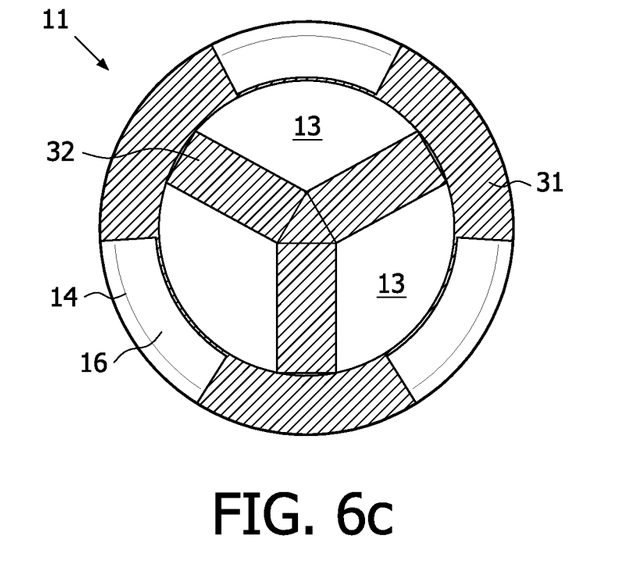
Figure 6D:
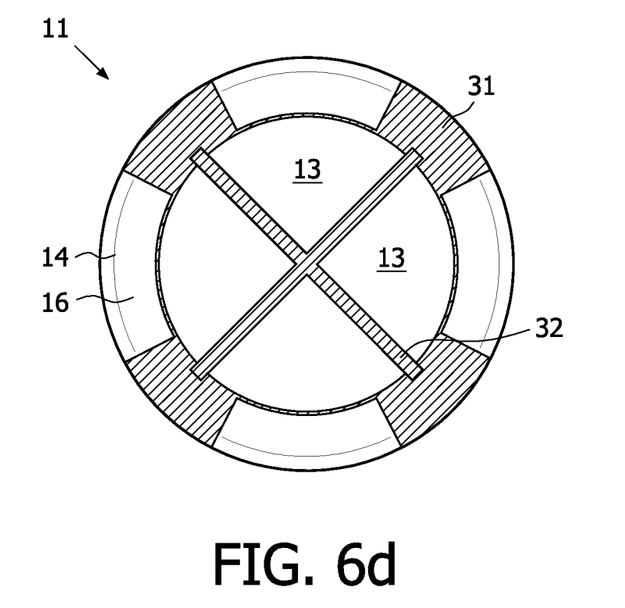

In FIGS. 6c and 6d, the drug compartment 13 is divided into three or four drug compartment 13. In these embodiments, each drug compartment 13 has at least one delivery window 16. Alternatively, two or more drug compartments 13 may share a delivery window 16, which may be useful if separate storage is important, but the drugs can be delivered simultaneously.

Figure 7A:
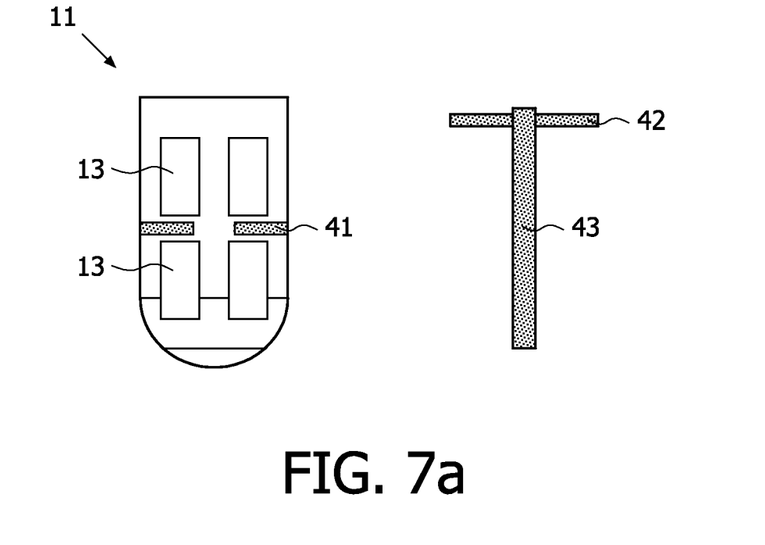
FIGS. 7a and 7b show cross section of another capsule with multiple compartments.
Figure 7B:
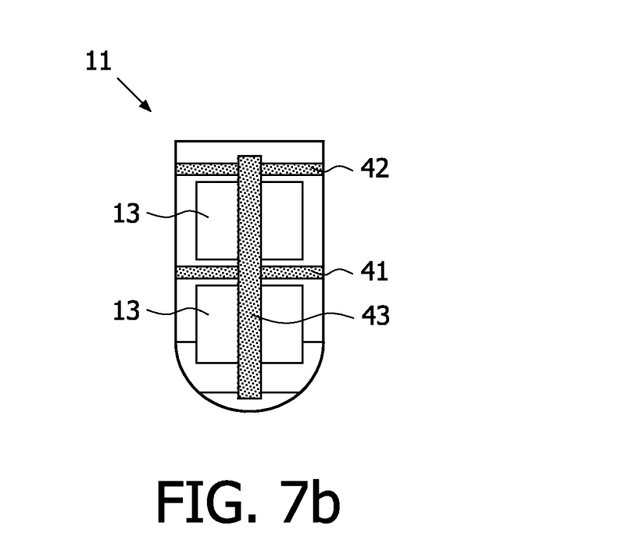

In FIGS. 6a-d, the drugs compartments 13 were only divided radially. In FIG. 7a a cross section is shown of a capsule with radially and axially divided drug compartments 13. An axial division of the drug compartments 13 is provided by a radial separation wall 41. The radial separation wall 41 has a hole in its center to allow filling of all drug compartments 13. An axial separation wall 43 is attached to the closing lid 42. After filling of the drug compartments, the lid 42 and the axial separation wall 43 are placed. The result is shown in FIG. 7b. FIG. 7b shows the filled first module 11, ready for connection to a second module 12.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An ingestible capsule for delivery of a drug, the capsule comprising:
    a first module comprising:
        a sidewall defining a drug compartment for containing an amount of the drug,
        a window formed as an opening through the sidewall of the drug compartment;
        a foil fixed to the sidewall of the drug compartment and covering the window,
        a conducting heating wire contacting the foil,
        an indicator conducting trace across the conducting heating wire, and
        at least one first conductive element electrically connected to the conducting heating wire, and
    a second module comprising:
        a power source;
        electronics in communication with the power source for controlling an electrical pulse, and
        at least one second conductive element electrically connected to the power source,
    wherein securing the first module to the second module electrically connects the first conductive element and the second conductive element to electrically couple the heating wire to the electronics, and
    wherein the conducting heating wire is configured to break the foil with an applied current and breaking the foil causes the indicator conducting trace to open at the portion extending across the conducting heating wire, the opening of the indicator conducting trace indicating that the conducting heating wire has broken the foil.

2. An ingestible capsule as claimed in claim 1, further comprising a sliding contact for securing the first module to the second module.

3. An ingestible capsule as claimed in claim 1, further comprising a set of pins and sockets for securing the first module to the second module.

4. An ingestible capsule as claimed in claim 1, further comprising a screw thread for securing the first module to the second module.

5. An ingestible capsule as claimed in claim 1, wherein the electronics comprise at least one capacitor for increasing an intensity of the electrical pulse.

6. An ingestible capsule as claimed in claim 1, wherein an inner wall of the drug compartment is provided with an anti-sticking layer.

7. An ingestible capsule as claimed in claim 1, wherein the foil comprises a plastic.

8. An ingestible capsule as claimed in claim 7, wherein the plastic comprises low density polyethylene (LDPE).

9. An ingestible capsule as claimed in claim 1, wherein the foil is covered with Polychlorotrifluorethylene (PFTE).

10. An ingestible capsule as claimed in claim 1, wherein the heating wire is a printed electrically conducting trace.

11. An ingestible capsule as claimed in claim 1, wherein the indicator trace is electrically connected to the electronics.

12. An ingestible capsule as claimed in claim 1, wherein the first module comprises more than one drug compartment for comprising the amount of the drug, each drug compartment being sealed by a separate foil with an embedded conducting heating wire, the first conductive element being arranged for separately coupling each one of the heating wires to the electronics.

13. An ingestible capsule for delivery of a drug, the capsule comprising:
a first module comprising:
a first sidewall comprising an outer surface of the first module and defining a drug compartment,
a window formed as an opening through the first sidewall;
a polymer foil covering the window to prevent drug in the drug compartment from exiting through the window,
a metallic conducting heating wire embedded in the polymer foil,
a first connector at a termination of the first sidewall, and
a first conductive element disposed on the first connector and electrically connected to the conducting heating wire, and
a second module comprising:
a second sidewall comprising an outer surface of the second module and defining a volume,
a power source disposed in the volume;
electronics in the volume and in communication with the power source,
a second connector at a termination of the second sidewall and configured to cooperate with the first connector to secure the second module to the first module, and
a second conductive element disposed on the second connector and electrically connected to the power source,
wherein cooperation of the first connector with the second connector to secure the second module to the first module electrically connects the first conductive element and the second conductive element to electrically couple the heating wire to the electronics.

14. The ingestible capsule of claim 13, wherein the first connector is a first sliding contact upon which the first conductive element is disposed and the second connector is a second sliding contact upon which the second conductive element is disposed.

15. The ingestible capsule of claim 13, wherein the first connector is a first thread, the second connector is a second thread, the first conductive element is disposed in the first thread, and the second conductive element is disposed in the second thread.

16. The ingestible capsule of claim 13, further comprising an indicator trace positioned orthogonal to the heating wire.

17. The ingestible capsule of claim 13, the first module further comprising a lid proximate the termination of the sidewall to seal the drug compartment.

18. An ingestible capsule for delivery of a drug, the capsule comprising:
a first module comprising:
a sidewall defining an internal volume
a separation wall separating the internal volume into a first drug compartment and a second drug compartment,
a first window formed as an opening through the sidewall proximate the first drug compartment, placing the first drug compartment in fluid communication with an exterior of the capsule,
a second window formed as an opening through the sidewall proximate the second drug compartment, placing the second drug compartment in fluid communication with the exterior of the capsule;
a first foil covering the first window to seal the first drug compartment,
first conducting heating wire contacting the first foil,
a second foil covering the second window to seal the second drug compartment,
a second conducting heating wire contacting the second foil,
at least one first conductive element electrically connected to at least one of the first conducting heating wire or the second conducting heating wire,
an indicator conducting trace across the first conducting heating wire; and
a second module comprising:
a power source;
electronics in communication with the power source for controlling an electrical pulse, and
at least one second conductive element electrically connected to the power source,
wherein securing the first module to the second module electrically connects the first conductive element and the second conductive element to electrically couple the first and second conducting heating wires to the electronics, and
wherein the first conducting heating wire is configured to break the first foil with an applied current and breaking the first foil causes the indicator conducting trace to open at the portion extending across the first conducting heating wire, the opening of the indicator conducting trace indicating that the first conducting heating wire has broken the first foil.

19. The ingestible capsule of claim 18, the first module further comprising a lid disposed in an axial opening proximate a termination of the sidewall to seal the drug compartments.

* * * * *